United States Patent
Grant et al.

(10) Patent No.: US 11,160,906 B2
(45) Date of Patent: Nov. 2, 2021

(54) INJECTABLE NANOMATERIAL-EXTRACELLULAR MATRIX CONSTRUCTS

(71) Applicant: The Curators of the University of Missouri, Columbia, MO (US)

(72) Inventors: Sheila Ann Grant, Columbia, MO (US); David Grant, Columbia, MO (US); Daniel Grant, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 650 days.

(21) Appl. No.: 15/999,750

(22) PCT Filed: Feb. 21, 2017

(86) PCT No.: PCT/US2017/018732
§ 371 (c)(1),
(2) Date: Aug. 20, 2018

(87) PCT Pub. No.: WO2017/143344
PCT Pub. Date: Aug. 24, 2017

(65) Prior Publication Data
US 2021/0220521 A1    Jul. 22, 2021

Related U.S. Application Data

(60) Provisional application No. 62/296,975, filed on Feb. 18, 2016.

(51) Int. Cl.
*A61L 27/10* (2006.01)
*A61L 27/50* (2006.01)
(Continued)

(52) U.S. Cl.
CPC .............. *A61L 27/50* (2013.01); *A61L 27/10* (2013.01); *A61L 27/16* (2013.01); *A61L 27/365* (2013.01);
(Continued)

(58) Field of Classification Search
None
See application file for complete search history.

(56) References Cited

U.S. PATENT DOCUMENTS

| 2005/0013870 A1 | 1/2005 | Freyman et al. |
| 2005/0181016 A1 | 8/2005 | Freyman et al. |

(Continued)

FOREIGN PATENT DOCUMENTS

| WO | 2010/099463 A2 | 9/2010 |
| WO | 2013/142308 A1 | 9/2013 |

OTHER PUBLICATIONS

"Measuring the Different Types of Viscosity with Viscometers" by M. Bonner (2017; 6 pages), (Year: 2017).*

(Continued)

*Primary Examiner* — Ernst V Arnold
(74) *Attorney, Agent, or Firm* — Stinson LLP (57) ABSTRACT

The present invention provides a series of injectable bio-nanocomposites that may be delivered via injection to various tissue repair sites including myocardial infarction, intervertebral disc reconstruction, reconstruction of skeletal muscle, and musculoskeletal applications, urinary incontinence, adipose tissue engineering, and orthopedic applications such as osteoporosis, and meniscus and articular cartilage repair.

17 Claims, 6 Drawing Sheets

(51) Int. Cl.
*A61L 27/36* (2006.01)
*A61L 27/16* (2006.01)
*B82Y 5/00* (2011.01)

(52) U.S. Cl.
CPC ....... *A61L 27/3633* (2013.01); *A61L 27/3691* (2013.01); *A61L 2400/06* (2013.01); *A61L 2400/12* (2013.01); *A61L 2430/30* (2013.01); *A61L 2430/38* (2013.01); *B82Y 5/00* (2013.01)

(56) References Cited

U.S. PATENT DOCUMENTS

| | | |
|---|---|---|
| 2008/0027542 A1 | 1/2008 | McQuillan et al. |
| 2010/0106233 A1 | 4/2010 | Grant et al. |
| 2010/0143487 A1 | 6/2010 | Masters |
| 2010/0185219 A1 | 7/2010 | Gertzman et al. |
| 2010/0222882 A1 | 9/2010 | Badylak et al. |
| 2011/0151011 A1 | 6/2011 | Flynn |
| 2013/0053960 A1 | 2/2013 | Park et al. |
| 2013/0195752 A1 | 8/2013 | Panyam et al. |
| 2013/0288375 A1* | 10/2013 | Zhang ................ C12N 5/0068 435/397 |
| 2014/0178450 A1 | 6/2014 | Christman et al. |
| 2014/0302104 A1 | 10/2014 | Harris et al. |
| 2015/0289967 A1 | 10/2015 | Grant et al. |
| 2016/0038643 A1 | 2/2016 | Detamore et al. |

OTHER PUBLICATIONS

International Search Report relating to PCT Application No. PCT/US2017/018732 dated May 15, 2017, 4 pages.
Written Opinion relating to PCT Application No. PCT/US2017/018732 dated May 15, 2017, 8 pages.
Choi, "Decellularized Extracellular Matrix Derived from Porcine Adipose Tissue as a Xenogeneic Biomaterial for Tissue Engineering", published Jul. 2012, vol. 18, No. 11, pp. 1-11.
Deeken, "Characterization of bionanocomposite scaffolds comprised of mercaptoethylamine-functionalized gold nanoparticles cross-linked to acellular porcine tissue", published Nov. 2011, J. Mater Sci: Mater Med 23:537-546.
Deeken, Grant, "Assessment of the biocompatibility of two novel, bionanocomposite scaffold in a rodent model," Journal of Biomedical Materials Research B: Applied Biomaterials (Feb. 2011) vol. 96B, Issue 2, pp. 351-359.
Grant, "Assessment of the biocompatibility and stability of a gold nanoparticle collagen bioscaffold", Journal of Biomedical Materials Research A (Feb. 2014) vol. 102A, Issue 2, pp. 332-339.
Mondalek, "The incorporation of poly(lactiv-co-glycolic) acid nanoparticles into porcine small instestinal submucosa biomaterials", Biomaterials 29 (2008) pp. 1159-1166.

* cited by examiner

INJECTABLE NANOMATERIAL-EXTRACELLULAR MATRIX CONSTRUCTS

CROSS-REFERENCE TO RELATED APPLICATION

This application is a 371 US National Patent Application which claims priority to PCT Patent Application No. PCT/US2017/018732 filed Feb. 21, 2017, which claims priority to U.S. Provisional Patent Application No. 62/296,975 filed on Feb. 18, 2016, the disclosure of which is incorporated herein by reference in its entirety.

FIELD OF THE INVENTION

The present invention relates to implant materials, methods of fabrication, and applications thereof. More specifically, the present invention relates to a series of biocompatible materials that can be injectable into soft tissues of a living body.

BACKGROUND OF THE INVENTION

The statements in this section merely provide background information related to the present disclosure and may not constitute prior art.

Extracellular matrix ("ECM") based scaffolds are becoming increasingly popular in musculoskeletal tissue engineering. (Brown B N, et al. Transl. Res. 163:268-85) These decellularized scaffolds have a lower inflammatory response and improved cellular integration compared to synthetic materials. (Badylak S F, et al. Acta Biomater. 5:1-13) In addition, the ECM contains cytokines and growth factors such as transforming growth factor beta, keratinocyte growth factor, and platelet derived growth factor that promote constructive tissue remodeling as the ECM naturally degrades. Degraded ECM products have also been shown to have chemotactic properties for fibroblasts and for some macrophages which may enhance ECM production. ECM contains points of cellular attachment providing an ideal environment for proliferation. The inventors' previous works described in the U.S. patent application Ser. No. 12/562,978 to Grant, et al., also disclosed an EMC as a bionanocomposite-comprising a decellularized tissue and a nanomaterial functionalized with surface functional groups capable of bonding with the tissue, wherein the nanomaterial is crosslinked with the decellularized tissue and the decellularized tissue has a tensile strength measured at yield ranging from 16 Mpa to 25 MPa. However, despite of many benefits of using ECM based graft materials, their application can be limited due to their form as a graft material.

Therefore, there is a need to provide an ECM based material that can be delivered by injection to expand the benefits of ECM to a wider variety of applications.

SUMMARY OF THE INVENTION

The present invention provides injectable bionanocomposite comprising a homogenized nanomaterial-bioscaffold, wherein the bioscaffold comprises a decellularized tissue, the decellularized tissue being conjugated with a nanoparticle, whereby the bionanocomposite has a viscosity ranging from about 100 cps to about 25,000 cps.

Further, the invention is also directed to an injectable ECM-based tissue construct (i.e., injectable bionanocomposite) that can be employed in various tissue engineering applications. The inventive injectable bionanocomposite comprises a homogenized nanoparticle-bioscaffolds that further comprising decellularized tissue conjugated with nanomaterials, whereas such bionanocomposite has a viscosity ranging from 100 cps to 10,000 cps.

The invention is further directed to a method of treating osteoarthritis comprising administering an effective amount of the bionanocomposite described herein to a subject in need thereof by injection into the affected area. Preferably, the osteoarthritis is post-traumatic osteoarthritis.

Another aspect of the invention is a method of treating tissue degradation comprising administering an effective amount of the bionanocomposite described herein to a subject in need thereof by injection to the subject's heart, disc, muscle, urinary tract, adipose tissue, meniscus, ligament, tendon, or a combination thereof.

The invention also provides a method of fabricating the injectable bionanocomposite. The inventive fabrication method comprises decellularizing a biological tissue to produce a piece of decellularized tissue, conjugating the decellularized tissue with a nanomaterial to produce a nanoparticle-bioscaffold, and homogenizing the nanoparticle-bioscaffold to produce an injectable bionanocomposite with a viscosity from about 100 cps to about 25,000 cps.

Further methods for functionalizing various nanoparticles, (e.g., gold and silver) are used before conjugating the nanoparticles to the decellularized tissue, while other nanoparticles (e.g., hydroxyapatite) do not need to be functionalized before conjugation.

The invention further provides a variety of applications of the inventive injectable bionanocomposite. The inventive injectable bionanocomposite may be delivered via injection to various tissue repair sites including myocardial infarction, intervertebral disc reconstruction, reconstruction of skeletal muscle, and musculoskeletal applications, urinary incontinence, adipose tissue engineering, and orthopedic applications such as osteoporosis, and meniscus and articular cartilage repair.

BRIEF DESCRIPTION OF THE DRAWINGS

The drawings described herein are for illustration purposes only and are not intended to limit the scope of the present teachings in any way.

Corresponding reference numerals indicate corresponding parts throughout the several views of drawings.

DETAILED DESCRIPTION

The present disclosure provides a new and improved bionanocomposites that be delivered via injection to various tissue repair sites. The injectable bionanocomposite is a homogenized metallic, ceramic, and/or polymeric nanomaterial-bioscaffold composed of decellularized tissue conjugated with metallic, ceramic or polymeric nanoparticles, and the injectable bionanocomposite has a viscosity ranging 100 to 25,000 cps. Any tissue, which is suitable for the bionanocomposite described in the inventors' previous U.S. patent application Ser. No. 12/562,978 (published as U.S. Patent Application Publication No. 2010/0106233), may be employed for the present injectable bionanocomposite. The nanoparticles can be a metallic, a ceramic or a polymeric nanomaterial, which is suitable for the bionanocomposite of U.S. Patent Application Publication No. 2010/0106233.

The advantage of injectable bionanocomposites over conventional ECM implant materials are homogenized scaffolds i) can conform to the repair site (such as wound bed or defect) to allow complete coverage and contact with the repair site; and ii) can be injected through hypodermic syringes or cannulas to the site of the fracture (or ligament/tendon tear) without open surgery, reducing the risk of infection during operation. Particularly, an injectable ECM-AuNP has been developed for musculoskeletal tissue engineering applications. More specifically, AuNP were amine-functionalized and conjugated to decellularized porcine diaphragm tendon. The tissue was then homogenized into an injectable form to be delivered to the defect. In addition to the benefits of ECM and AuNP as previously known, there are several benefits to using a combined ECM/AuNP construct. By conjugating the AuNP to the ECM, the native microstructure of the ECM is maintained while enhancing stability and allowing cellular integration. The crosslinking treatment used in the conjugation of AuNP slows tissue degradation which allows additional time for neo-cartilage formation and longer lasting anti-inflammatory effects. AuNP are conjugated to tissue to prevent "wash-out" and to maintain effectiveness for longer periods of time compared to attachment by nanoparticle adsorption to the tissue. By homogenizing the tissue, the benefits of ECM and AuNP can be delivered to the defect site in an injectable form.

The present invention further provides a general fabrication method for the abovementioned injectable bionanocomposite. The inventive fabrication method comprises the step of decellularizing a biological tissue to produce a decellularized tissue, conjugating the decellularized tissue with a nanoparticle to produce a nanoparticle-bioscaffold, and homogenizing said nanoparticle-bioscaffold to a specified viscosity range. When metallic nanomaterials, such as gold and silver, are employed, the fabrication method may further include the optional functionalizing step before the aforesaid conjugating step. The optional functionalizing step comprises functionalizing preselected nanoparticles with surface functional groups capable of bonding the decellularized tissue.

Decellularized Tissue

The decellularized tissue can be a variety of materials including a meniscus, a tendon, a ligament, a diaphragm, or a combination thereof.

The decellularized tissue can be porcine, or human tissue.

The decellularized tissue may be obtained from treatment of biological tissue, that can be harvested from either allograft or xenograft. The tissue is decellularized in that cells and cellular remnants are removed while the extracellular matrix components remains intact. A variety of biological tissue donor sources may be employed, such as human (dermis, tensor fascia lata, blood vessels, and amniotic membrane), porcine (small intestine submucosa, dermis, blood vessels, and bladder), bovine (dermis, blood vessels, and pericardium), and equine (blood vessels and pericardium), which have been studied for other purposes. Many of these materials provide desirable degradation characteristics and when implanted either alone or once crosslinked to nanoparticles, can release growth factors and peptides that possess antimicrobial properties, enhance angiogenesis, and aid tissue remodeling by attracting endothelial and bone marrow-derived cells to the implant site.

In many instances, the tissue may be selected according to its compatibility for the use of the injectable bionanocomposite. For example, if repair of a meniscus is desired, a decellularized meniscus would preferably be used to prepare the injectable bionanocomposite for that purpose. To that end, a decellularized tendon would be used in an injectable bionanocomposite to repair a tendon, a decellularized ligament would be used in an injectable bionanocomposite to repair a ligament, and the like.

For commercialization purposes, a user may also consider whether large quantities of the tissue can be easily obtained and processed.

The selected biological tissue is processed to remove native cells, i.e. "decellularized" in order to prevent an immune response when it is utilized as a soft tissue repair material. (Gilbert et al. Decellularization of tissues and organs. Biomaterials 2006; 27:3675-3683) The decellularization process can be optimized for each species and type of tissue. Successful decellularization is characterized by the removal of cellular nuclei and remnants with the retention of natural extracellular matrix components (collagen, elastin, growth factors, etc.) and overall tissue structure (collagen architecture). (Gilbert et al.) For example, from about 80% to 100%, from about 85% to about 100%, from about 90% to about 100%, or from about 95% to about 100% of the cellular nuclei and remnants are removed from the tissue. Further, the decellularized material can contain from about 0.1% to about 20%; from about 0.1% to about 15%; from about 0.1% to about 10%; from about 0.1% to about 5% of the original cellular material after decellularization.

The collagen structure can be advantageous for cell attachment and infiltration. Thus, maintaining the collagen structure can be desirable during the decellularization process. For example, the collagen structure has pore size from about 1 nm to about 100 nm. Further, the collagen structure has a porosity of from about 10% to about 90%; from about 20% to 90%; from about 30% to about 90%; from about 30% to about 80%; or from about 40% to about 80%.

The decellularizing process can take the form of physical (sonication, freezing, agitation, etc.), chemical (acids, ionic, non-ionic, and zwitterionic detergents, organic solvents, etc.), and enzymatic (protease, nuclease, etc.) treatments or a combination thereof and can employ any procedure commonly practiced in the field. (Gilbert et al.) Physical methods for decellularization include freezing, direct pressure, sonication, and agitation; these methods need to be modified depending on the particular tissue. Chemical methods include treatment with an acid, a base, a non-ionic detergent, an ionic detergent, a zwitterionic detergent, an organic solvent, a hypotonic solution, a hypertonic solution, a chelating agent, or a combination thereof.

The acid or base solubilizes cytoplasmic components of cell and disrupts nucleic acids. Exemplary acids and bases are acetic acid, peracetic acid, hydrochloric acid, sulfuric acid, ammonium hydroxide or a combination thereof.

Treatment with non-ionic detergents disrupts lipid-lipid and lipid-protein interactions, while leaving protein-protein interactions intact. An exemplary non-ionic detergent is Triton X-100.

An ionic detergent solubilizes cytoplasmic and nuclear cellular membranes and tends to denature proteins. Exemplary ionic detergents are sodium dodecyl sulfate, sodium deoxycholate, Triton X-200, or a combination thereof.

A zwitterionic detergent treatment exhibits properties of on-ionic and ionic detergents. Exemplary zwitterionic detergents are 3-[3-cholamidopropyl)dimethylammonio]-1-propanesulfonate (CHAPS), sulfobetaine-10 (SB-10), sulfobetaine-16 (SB-16), or a combination thereof.

Tri(n-butyl)phosphate is an organic solvent that disrupts protein-protein interactions.

Chelating agents bind divalent metallic ions that disrupt cell adhesion to the extracellular matrix. Exemplary chelating agents are ethylenediamine tetraacetic acid (EDTA), ethylene glycol tetraacetic acid (EGTA), or a combination thereof.

The decellularization can also be carried out using enzymatic methods. Exemplary enzymes are trypsin, endonucleases, exonucleases, or a combination thereof. Trypsin cleaves peptide bonds on the C-side of arginine and lysine. Endonucleases catalyze the hydrolysis of the interior bonds of ribonucelotide and deoxyribonucleotide chains. Exonucleases catalyze the hydrolysis of the terminal bonds of ribonucleotide and deoxyribonucleotide chains.

The decellularization is performed by treatment with acetic acid, peracetic acid, hydrochloric acid, sulfuric acid, ammonium hydroxide, Triton X-100, sodium dodecyl sulfate, sodium deoxycholate, Triton X-200, 3-[3-cholamidopropyl)dimethylammonio]-1-propanesulfonate (CHAPS), sulfobetaine-10 (SB-10), sulfobetaine-16 (SB-16), tri(n-butyl)phosphate, EDTA, EGTA, or a combination thereof.

Generally, the decellularization process includes immersion of the desired tissue in an agent that can make the tissue acellular (i.e., the tissue contains no cells). The agent that makes the tissue acellular can be an acid, a solvent, a surface active agent, and the like. The concentration of the agent is from about 0.5% (v/v) to about 5% (v/v). The concentration of the agent can be from about 1% (v/v) to about 2% (v/v).

The tissue is immersed in the agent for about 6 hours to about 36 hours; from about 12 hours to about 30 hours; from about 18 hours to about 30 hours; or from about 20 hours to 28 hours.

The decellularization process can be performed at room temperature.

Preferably, the decellularization process can include immersion for 24 hours with agitation in the following solutions: (1) 0.1% (v/v) peracetic acid with 4% ethanol, (2) 1% (v/v) TritonX-100, (3) 1% (v/v) Triton X-100 with 1% (v/v) tributyl phosphate (TnBP), (4) 2% (v/v) TnBP, (5) 1% (v/v) TnBP, (6) 1% (w/v) sodium dodecyl sulfate (SDS), (7) 0.5% (w/v) SDS.

Further, a combination of both physical and chemical treatments can be employed. This process includes two substeps, decellularization and subsequent rinses. In the decellularization step, the selected biological tissue is submersed in a buffered solution containing an organic solvent, tri(n-butyl)phosphate (TnBP), with agitation, such as in an orbital shaker, for about 24 hours. The resulting tissue is then rinsed to remove residual solvent and cellular remnants. The rinsing solvents may be deionized water and about 70% ethanol consecutively for a period of time, such as about 24 hours each. The tissue:solution volume ratio is from about 1:500 to about 5:100; from about 1:200 to about 2:100; or about 1:100 throughout the decellularization and subsequent rinses.

Several tests may be employed to verify the effectiveness of the decellularization process, i.e., removal of all cells and cellular remnants such as DNA while leaving extracellular matrix (ECM') components (such as collagen, elastin, fibronectin, laminin, and glycosaminoglycans) intact. For example, a standard histological staining with hematoxylin and eosin (H&E) may be performed to identify any cell nuclei remaining in the resulting tissue. For example, the decellularized material desirably will be substantially free of cell nuclei and cellular remnants. Preferably, when a representative section of the decellularized material (1 cm×1 cm) is stained with H&E, the decellularized material will have less than about 20 cell nuclei remaining and be substantially free of cellular remnants wherein substantially free of cell nuclei and cellular remnants means less than 15; less than 12; less than 10; less than 8; or less than 5 nuclei or cell remnants in the field of view of the decellularized tissue. Further, the collagen structure of the decellularized material is substantially the same as the structure of the tissue before decellularization.

Finally, the decellularized tissue is biocompatible. The biocompatibility of the tissue can be measured using flow cytometry wherein cells incubated with the decellularized tissue did not show a significantly higher cell death rate as compared to the same cells under the same conditions but without contacting a tissue. A significantly higher cell death rate occurs when statistical significance ($p<0.05$) is measured. Microscopic analyses may be performed to verify that all fibroblasts and endothelial cells are successfully removed from the resulting tissue. Methyl green pyronin stain, which stains for DNA and RNA, may also be utilized to verify that remnants of DNA and RNA are effectively removed from the tissue during the extensive rinse sequence. Further histological analyses, such as Masson's Trichrome, Verhoeff-van Gieson, and Alcian Blue staining, may also be performed to verify that ECM components remain within the decellularized tissue.

Nanomaterials

The nanoparticle can be an amine-functionalized gold nanoparticle (AuNP), a hydroxyapatite nanoparticle, a silver nanoparticle, a ceramic nanoparticle, a polymeric nanoparticle, or a combination thereof. Preferably, the nanoparticle is an amine-functionalized gold particle.

Nanomaterials are conjugated to the decellularized tissue to form the bionanocomposite. Prior studies have demonstrated that nanomaterials are more hydrophilic and possess an increased number of atoms and crystal grains at their surface compared to conventional materials. The large number of grains at the surface leads to increased surface roughness, surface area, and surface energy which are thought to contribute to an increase in protein adsorption and unfolding. For example, nanoscale ceramics, metals, and polymers have all been shown to improve cellular function compared to conventional materials. Webster T J et al. J Biomed Mater Res 2000; 51:475-483; Price R L, et al. Journal of Biomedical Materials Research Part A 2003; 67A:1284-1293; Webster T J, et al. Biomaterials 2004; 25:4731-4739; Park G E, et al. Biomaterials 2005; 26:3075-3082; Thapa A, et al. Journal of Biomedical Materials Research Part A 2003; 67A:1374-1383; Christenson E M, et al. Journal of Orthopaedic Research 2007; 25:11-22.) These properties make nanomaterials ideally suited to enhance the biocompatibility and cell/tissue interaction with extracellular matrix-derived scaffolds.

The nanomaterials employed in the invention may be selected from a variety of nanomaterials that are nontoxic and biocompatible such as gold, silver, silicon carbide, a degradable polymer (polylactic acid/polyglycolic acid, polycaprolactone), a carbon nanotube, silicon, silica and a combination of coated nanomaterials. The nanomaterial can be a gold nanoparticle, a gold nanorod, a gold nanofiber, a silver nanoparticle, a silver nanorod, a silver nanofiber, a platinum nanoparticle, a platinum nanorod, a platinum nanofiber, a titania nanoparticle, a titania nanorod, a titania nanofiber (rutile structure, $Ti_2O_3$, $BaTiO_3$, and the like), a silicon nanoparticle, a silicon nanorod, a silicon nanofiber, a silica nanoparticle, a silica nanorod, a silica nanofiber, an alumina nanoparticle, an alumina nanorod, an alumina nanofiber, a calcium phosphate nanoparticle, a calcium phosphate nanorod, a calcium phosphate nanofiber, a hydroxyapatite nanoparticle, a hydroxyapatite nanorod, a hydroxyapatite nanofiber, a $BaTiO_3$ nanoparticle, a $BaTiO_3$ nanorod, a $BaTiO_3$ nanofiber, a polycaprolactone nanofiber, a polyglycolic acid nanofiber, a polylactic acid nanofiber, a polylacticglycolic acid nanofiber, a polydoxanone nanofiber, a trimethylene carbonate nanofiber, or a combination thereof. Various preferred nanomaterials are a gold nanoparticle, a gold nanorod, a gold nanofiber, a silver nanoparticle, a silver nanorod, a silver nanofiber, a hydroxyapatite particle, or a combination thereof.

Generally, the median diameter of the nanomaterials can be from about 1 nm to about 150 nm, from about 1 nm to about 120 nm, from about 1 nm to about 110 nm, from about 1 nm to about 100 nm, from about 10 nm to about 150 nm, from about 10 nm to about 120 nm, from about 10 nm to about 110 nm, from about 10 nm to about 100 nm, from about 20 nm to about 150 nm, from about 20 nm to about 120 nm, from about 20 nm to about 110 nm, or from about 20 nm to about 100 nm.

Further, the particle sizes for the nanoparticles can be polydisperse or monodisperse.

In the functionalizing step, the selected nanomaterials obtained commercially or synthesized according to various procedures in the field can be exposed to a plasma environment with selected plasma chemistry in order to introduce new functionalities which will enhance the bonding between the nanomaterials and tissue. Generally, the precursor selected for plasma polymerization is a molecule that has one or more of the desired functional groups and one or more carbon-carbon double bonds. For example, if the desired surface functional group is an amine, the precursor would contain an amine and a carbon-carbon double bond. Examples of amines that can be used in plasma polymerization are allylamine, poly(allylamine), diaminocyclohexane, 1,3-diaminopropane, heptylamine, ethylenediamine, butylamine, propargylamine, propylamine, and the like. In some embodiments, amines that can be used in plasma polymerization are poly(allylamine), diaminocyclohexane, 1,3-diaminopropane, heptylamine, ethylenediamine, butylamine, propargylamine, propylamine, and the like.

When the desired surface functional group is a carboxylic acid, the precursor would contain a carboxylic acid group and a carbon-carbon double bond. Examples of compounds used are acrylic acid, methacrylic acid, propanoic acid, and the like. When the desired surface functional group is a hydroxyl group, the precursor would contain a hydroxyl group and a carbon-carbon double bond. Examples are allyl alcohol, hydroxyethyl methacrylate, hydroxymethyl acrylate, hydroxybutyl methacrylate, and the like.

The functional groups, such as —$NH_x$ (x=1 or 2), —OH, —COOH, can be selected to act as anchoring points for crosslinking the decellularized tissue via covalent bond formation. A variety of plasma chemistry may be employed to introduce the functional groups. For example, allylamine may be used to deposit —NH, and, —$NH_2$ containing plasma coatings on the nanomaterial surfaces. Allyl alcohol, hydroxyethyl methacrylate (HEMA), acrylic acid, methacrylic acid, hydroxymethyl acrylate, hydroxybutyl methacrylate, or a combination thereof may be utilized as the monomers to deposit plasma coatings and introduce —OH, —COOH functional groups on nanomaterial surfaces. Additionally, organosilicons including trimethylsilane (3MS) and hexa-methyldisiloxane (HMDSO) may be used to plasma coat the nanomaterials to ensure excellent adhesion of plasma coating to nanowires. The organosilicon coating provides a layer on the nanomaterial that aids adhesion of the nanoparticle to the deposited functionalized coating. Subsequent plasma treatment using $O_2$ or $CO_2$ may be used to further increase the surface concentration of these functional groups.

Furthermore, nanomaterials may be functionalized via a chemical reaction utilizing an activating agent (e.g., an agent capable of activating a carboxylic acid); for example, dicyclohexyl carbodiimide, diisopropylcarbodiimide, or ethyl dimethylaminopropylcarbodiimide. The activating agent can be used alone or in combination with an agent that improves efficiency of the reaction by stabilizing the reaction product. Once such stabilization agent is NHS (N-hydroxysuccinimide). In various embodiments, EDC (1-ethyl-3-[3-dimethylaminopropyl]carbodiimide) and NHS (N-Hydroxysuccinimide) are used as the crosslinking agents wherein EDC reacts with the carboxylic acid groups found on nanomaterials such as degradable polymers and forms an O-acrylisourea derivative and NHS stabilizes this derivative and forms a succinimidyl ester bond, which allows binding to an amino group of the tissue by forming a covalent peptide bond with the nanomaterial. When EDC and NHS are used to functionalize the nanomaterials, the molar ratio of the agents range from about 1:5 EDC:NHS to about 5:1 EDC:NHS; or about 2:5 EDC:NHS. Alternatively, nanomaterials may be functionalized via aminolysis by ethylenediamine or N-Aminoethyl-1,3-propanediamine.

For the preferred nanomaterials of gold nanoparticles, gold nanorods, gold nanofibers, silver nanoparticles, silver nanorods, silver nanofibers, or combinations thereof, the nanomaterials can be functionalized by coordinating a ligand containing the desired functional group to the gold or silver atom. Generally, the ligand should have at least two functional groups; one of the functional groups can coordinate to the metal site and the other could be used to crosslink with the decellularized material. For example, a ligand having a thiol group and an amine group; e.g., cysteine, methionine, mercaptoalkylamines such as mercaptomethylamine, mercaptoethylamine (MEA), mercaptopropylamine, mercaptobutylamine, and the like, can be coordinated to the metal of the nanomaterial to provide a functional group for further reaction with the decellularized material. Also, a ligand having a thiol group and a carboxylic acid group; e.g., thiosalicylic acid, 2-mercaptobenzoic acid, can be coordinated to the metal of the nanomaterial to provide a functional group for further reaction with the decellularized material.

When the nanomaterial is silicon carbide, the silicon carbide nanomaterial can be treated with various reagents that have at least two functional groups; one group that can react with the surface hydroxy groups on the silicon carbide and another functional group that can crosslink to the decellularized material. For example, the silicon carbide particles can be reacted with aminoalkyl-trialkoxysilanes such as aminomethyl-trimethoxysilane, aminoethyl-trimethoxysilane, aminopropyl-trimethoxysilane, aminobutyl-trimethoxysilane, aminomethyl-triethoxysilane, aminoethyl-triethoxysilane, aminopropyl-triethoxysilane, aminobutyl-triethoxysilane, aminomethyl-tripropoxysilane, aminoethyl-tripropoxysilane, aminopropyl-tripropoxysilane, aminobutyl-tripropoxysilane, aminomethyl-tributoxysilane, aminoethyl-tributoxysilane, aminopropyl-tributoxysilane, aminobutyl-tributoxysilane, or a combination thereof to provide amine groups on the surface of the silicon carbide nanomaterial.

In various embodiments, the decellularized tissue alone or in the bionanocomposite retains its proteins, growth factors, and other peptides. For example, the decellularized tissue retains growth factors such as vascular endothelial growth factor (VEGF), transforming growth factor (TGF-B1), proteins such as collagen, elastic, fibronectin, and laminin, and other compounds such a glycosaminoglycans. Because the decellularization process does not remove these proteins, growth factors, and other peptides, the tissue or bionanocomposite comprising the decellularized tissue can release these factors during its remodeling and resorption by the body. This release is advantageous to cell growth and cell infiltration into the affected tissue. Therefore, retention of these compounds is advantageous for the implant material.

Optionally, in addition to the endogenous proteins, growth factors, and peptides that enhance cell adhesion, cell growth, and cell infiltration into the implant material, the functionalization step may include a substep to increase tissue integration, whereas the nanomaterials may be treated with exogenous cell adhesion proteins and/or peptides. The addition of these active group will promote better cellular adhesion, vascularization, and improve overall biocompatibility. The ECM proteins are important in cell adhesion. Cell adhesion to ECM proteins is mediated by integrins. Integrins bind to specific amino acid sequences on ECM proteins such as RGD (arginine, glycine, aspartic acid) motifs. Therefore there has been research conducted on the control of the orientation and conformation of cell adhesion proteins onto materials so that RGD motifs are accessible to integrins. For example, fibronectin and fibronectin-III have been adsorbed onto synthetic surfaces. The results showed that presence of fibronectin-III displayed more cell-binding domains than the fibronectin-free surface. Thus, it is possible to manipulate and specifically orient the cell binding proteins so that increased tissue integration is possible. Another in vivo study by Williams et al. (S. K. Williams, et al. Covalent modification of porous implants using extracellular matrix proteins to accelerate neovascularization. J Biomed Mater Res. 78A: 59-65, 2006) analyzed collagen type IV, fibronectin, and laminin type I's ability to promote peri-implant angiogenesis and neovascularization. Laminin stimulated extensive peri-implant angiogenesis and neovascularization into the porous ePTFE substrate material.

Additionally, vascular endothelial growth factor (VEGF) is a chemical signal secreted by cells to stimulate neovascularization. VEGF stimulates the proliferation of endothelial cells. TGF-B1 (transforming growth factor) is another chemical signal that stimulates the differentiation of myofibroblasts. Both types of growth factors have been incorporated into tissue engineered scaffolds to stimulate and accelerate reconstitution of native tissue.

The additional amines can be used as sites for attaching cell adhesion peptides, growth factors, glycosaminoglycans, or anti-inflammatory medications to further improve the biocompatibility of the scaffold.

Conjugating Nanomaterial to Decellularized Tissue

Conjugating of the nanomaterial to the decellularized tissue is joining the two components by a covalent bond. Conjugating reagents are molecules that contain two or more reactive ends capable of chemically attaching to specific functional groups on proteins or other molecules (e.g., decellularized tissue). These functional groups can be amines, carboxyls, or sulfhydryls on the decellularized tissue. To react with amines in the tissue, the conjugating agent is selected from N-hydroxysuccinimide ester (NHS ester), N-gamma-maleimidobutyryloxy succinimde (GMBS), imidoester (e.g., dimethyl adipimidate, dimethyl pimelimidate, dimethylsuberimidate, dimethyl 3,3'-dithiobispropionimidate.2 HCl (DTBP)), pentafluorophenol ester (PFP ester), hydroxymethyl phosphine. A carboxyl group on the tissue can react with an amine on the nanoparticle directly by activation with carbodiimide. Various carbodiimides can be used including 1-ethyl-3-(3-dimethylaminopropyl)carbodiimide, dicyclohexyl carbodiimide, diisopropylcarbodiimide, and the like. A sulfhydryl group on the tissue can react with a malemide (e.g., N-e-Maleimidocaproic acid (EMCA)), haloacetyl (e.g., SBAP (NHS ester/bromoacetyl), SIA (NHS ester/iodoacetyl), SIAB (NHS ester/iodoacetyl), Sulfo-SIAB (sulfo-NHS ester/iodoacetyl), pyridyldisulfide (1,4-di(3'-(2'-pyridyldithio)-propionamido)butane (DPDPB), sulfosuccinimidy 6-(3'-[2-pyridyldithio]-propionamido)hexanoate (Sulfo-LC-SPDP), N-[4-(p-azidosalicylamido)butyl]-3'-(2'-pyridyldithio)propionamide (APDP)), or vinyl sulfone.

In some cases the nanomaterials do not require additional functionalization and can be conjugated to the decellularized tissue without the additional functionalization step. For example, hydroxyapatite nanomaterials can be conjugated to the decellularized tissue without additional functionalization of the hydroxyapatite nanoparticle.

In the conjugation step, depending on the surface functional groups introduced, the functionalized nanomaterials are incubated (or mixed) with the decellularized tissues in a solution via a procedure available or known to the researchers in the field. The conjugating agent can be N-gamma-maleimidobutyryloxy succinimde (GMBS), N-e-Maleimidocaproic acid (EMCA), and Dimethyl 3,3'-dithiobispropionimidate.2 HCl (DTBP). For example, according to one embodiment, the crosslinking solution may contain acetone, 1x PBS (phosphate buffered saline), EDC (1-ethyl-3-[3-dimethylaminopropyl]carbodiimide) and NHS (N-Hydroxysuccinimide). For the conjugating reaction, a tissue:solution volume ratio of from about 1:100 to about 20:100; from about 5:100 to about 15:100; from about 7:100 to about 10:100; or an 8:100 ratio is maintained and for rinsing, a tissue:solution volume ratio from about 0.1:100 to about 10:100; from about 0.5:100 to about 2:100; or 1:100 ratio is maintained for all subsequent rinses.

Various concentrations of nanomaterials may be utilized to achieve optimal crosslinking. The incubation generally lasts about 24 hours at room temperature on an orbital shaker table at low rpm. Following incubation, the resulting crosslinked tissues are vigorously rinsed with 1×PBS for 48 hours on an orbital shaker table with several changes of the PBS solution to remove residual crosslinkers and unbound nanomaterials. Crosslinked tissues are then stored in 1×PBS at 4° C. until subsequent testing or sterilization occurs.

The injectable bionanocomposites can be prepared using nanoparticles having a median diameter from about 20 nm to about 100 nm.

A concentration of nanoparticles in the conjugation reaction having a median diameter from about 20 nm to about 30 nm can be from about $5 \times 10^{11}$ particles per mL to about $8 \times 10^{12}$ particles per mL, from about $7 \times 10^{11}$ to about $3 \times 10^{12}$ particles per mL, or from about $1 \times 10^{12}$ particles per mL to about $8 \times 10^{12}$ particles per mL. Preferably, the concentration of nanoparticles in the conjugation reaction having a median diameter from about 20 nm to about 30 nm can be from about $7 \times 10^{11}$ particles per mL to about $6 \times 10^{12}$ particles per mL.

The nanoparticles having a median diameter from about 20 nm to about 30 nm can be gold nanoparticles.

The injectable bionanocomposites can be prepared using nanoparticles having a median diameter from about 90 nm to about 100 nm and a concentration of nanoparticles in the conjugation can be from about $5 \times 10^{9}$ particles per mL to about $5 \times 10^{10}$ particles per mL, from about $5 \times 10^{9}$ particles per mL to about $3 \times 10^{10}$ particles per mL, from about $5 \times 10^{9}$ particles per mL to about $2 \times 10^{10}$ particles per mL, or from about $5 \times 10^{9}$ particles per mL to about $1.4 \times 10^{10}$ particles per mL.

The nanoparticles having a median diameter from about 90 nm to about 1000 nm can be gold nanoparticles.

Homogenization

Many different methods can be used to homogenize the nanomaterial-bioscaffold to produce the injectable bionanocomposite. A person of skill would have understood that the variety of homogenization methods known in the art would be useful to provide a homogenized injectable bionanocomposite. In particular, methods that grind, shear, beat, and shock the nanomaterial-bioscaffold would be appropriate for the homogenization.

A mortar and pestle, cryogrinder, glass homogenizer, bead vortexer, or the like can be used to grind the nanomaterial-bioscaffold.

A blender, roto-stator, Dounce homogenizer, a Potter-Elvehjem with PTFE pestle, or french press can be used for shearing the nanomaterial-bioscaffold.

An amalgamator for tubes or a high throughput homogenizer can be used to beat the nanomaterial-bioscaffold.

A sonicator can be used to shock the nanomaterial-bioscaffold.

A viscosity-altering agent can be added when homogenizing the nanomaterial-bioscaffold. The viscosity-altering agent can be glycerin, ethylene diamine tetraacetic acid, hyaluronic acid, gellan gum, mannitol, guar gum, locust bean gum, xanthan gum, or a combination thereof. Preferably, the viscosity-altering agent is glycerin, ethylene diamine tetraacetic acid, hyaluronic acid, or a combination thereof.

The viscosity-altering agent can be added at a concentration of from about 1 wt. % to about 15 wt. % based on the total material in the homogenizing step. Preferably, the viscosity-altering agent is added at a concentration of from about 3 wt. % to about 10 wt. %.

Once the nanomaterial-bioscaffold construct is homogenized to make the injectable bionanocomposite, an additional agent can be added to the injectable bionanocomposite. The additional agent can be curcumin, chitin, or a combination thereof.

Injectable Bionanocomposite

The injectable bionanocomposite can have a viscosity ranging from about 100 cps to about 25,000 cps, from about 100 cps to about 20,000 cps, from about 100 cps to about 10,000 cps, from about 5,000 cps to about 20,000 cps, from about 5,000 cps to about 15,000 cps, from about 8,000 cps to about 25,000 cps, from about 8,000 cps to about 20,000 cps, or from about 8,000 cps to about 15,000 cps.

The injectable bionanocomposite can have the denaturation temperature of the bionanocomposite increase upon conjugation with a nanoparticle as compared to decellularized tissue not conjugated with a nanoparticle.

The injectable bionanocomposite can have an extrusion force measured in a 20-gauge cannula be from about 0.5 N to about 10 N, from about 0.5 N to about 5 N, or from about 1 N to about 4 N.

The injectable bionanocomposite can have a cell viability measured using a dsDNA assay be increased as compared to decellularized tissue not conjugated with a nanoparticle.

Uses

The invention further provides a variety of applications of the injectable bionanocomposites. Many injuries result in inflammatory response that can cause scarring or cellular destruction. The injectable bionanocomposites can be injected into the affected area to reduce the inflammation and reduce scarring and cellular destruction that results from the injury.

Particularly, the injectable bionanocomposites can be delivered via injection to various tissue repair sites including myocardial infarction, intervertebral disc reconstruction, reconstruction of skeletal muscle, musculoskeletal applications, urinary incontinence, adipose tissue engineering, and orthopedic applications such as osteoporosis, and meniscus and articular cartilage repair.

Further, the injectable bionanocomposites can be injected into the affected area to treat osteoarthritis. Preferably, the osteoarthritis is post-traumatic osteoarthritis.

Joint injury or trauma can result in acute post-traumatic osteoarthritis (PTOA). PTOA is characterized by joint swelling, synovial effusion, inflammatory cell infiltration, and chronic pain. Articular cartilage degeneration is a result of PTOA which can lead to osteoarthritis (OA) in the majority of patients with joint injury. The treatment of PTOA is challenging and there are not approved therapies to cure acute post-traumatic arthritis, only therapies that address the symptoms of PTOA are available. Injection of the bionanocomposites described herein can reduce inflammation and treat the underlying mechanisms resulting in the osteoarthritis.

The affected area can be a joint. Preferably, the joint is a knee, an ankle, a hip, a wrist, an elbow, a knuckle, a shoulder, or a combination thereof.

This description is merely exemplary in nature and is in no way intended to limit the present teachings, application, or uses. Throughout this specification, like reference numerals are used to refer to like elements.

EXAMPLE

Preparation of Injectable ECM-AuNP Constructs.

Tissue Harvest and Decellularization.

Porcine tissue was harvested immediately after euthanization. The central diaphragm tendon was dissected from surrounding tissue and stored in Tris Buffer solution consisting of 5 mM ethylenediaminetetraacedic acid (EDTA), 0.4 mM phenylmethylsulfonyl (PMSF), and 0.2% (w/v) sodium azide (pH=8.0) at 4° C. Tissue was decellularized in a 1% (v/v) tri(n-butyl) phosphate (TnBP) and Tris buffer solution for 24 hours according to previously established protocol. This was followed by two 24 hour rinses in deionized water and a 24 hour rinse in 70% (v/v) ethyl alcohol.

Conjugation of Nanomaterials.

Nanoparticles were purchased from Ted Pella, Inc. (Redding, Calif.). Concentrations refer to concentration of nanoparticles used in crosslinking procedure relative to the initial concentration given by the supplier. One times (1x) concentration refers to $7.0 \times 10^{11}$ particles per mL for 20 nm AuNP and to $5.6 \times 10^9$ particles per mL for 100 nm AuNP. Four times (4x) and eight times (8x) concentration are 4 and 8 times as concentrated as 1x concentrations, respectively. Attachment of AuNP to tissue was conducted according to a previously established protocol. AuNP were functionalized with 15 µM 2-mercaptoethylamine (MEA) prior to conjugation. Tissue was incubated for 15 minutes in crosslinking solution containing 50:50 (v/v) solution of acetone and 1x phosphate buffered saline (PBS) (pH=7.5) with 2 mM 1-ethyl-3-[3-dimethylainopropyl] carbodiimide (EDC) first dissolved in 0.1M 2-(N-Morpholino) ethanesulfonic acid (MES) in 0.5M sodium chloride (NaCl) (pH=6.0) and 5 mM N-hydroxysuccinimide (NETS) first dissolved in dimethylformamide (DMF). Tissue was removed from crosslinking solution and specified concentration of AuNP were added to cover tissue. After 2 hours, tissue was rinsed twice in 1xPBS for 24 hours each. The tissue group denoted as "crosslinked" received crosslinking treatment without the addition of the nanoparticle solution. The tissue group denoted as "decellularized" did not receive crosslinking treatment. Tissue groups are labeled according to their crosslinking treatment, AuNP size, and AuNP concentration. For example, tissue constructs conjugated with 20 nm AuNP at a 4x concentration are referred to as 4x20 nm constructs.

Tissue Homogenization.

Tissue sections in 1xPBS were placed in a Tissue Lyser II (Qiagen, Hilden, Germany) with stainless steel beads for 15 minutes at 30 Hz. Tissue was further homogenized using a blade homogenizer on ice. Homogenized tissue was stored in 1xPBS at 4° C. When ready for analysis, tissue was centrifuged to sediment tissue at bottom of tube and supernatant was removed. Centrifugation and decanting were repeated and homogenized tissue was stirred.

Sterilization.

Homogenized tissue was sterilized in sterilization solution containing 0.1% (v/v) peracetic acid (pH~7). Sterilization solution was passed through a 0.22 µm sterile filter unit before being added to homogenized tissue. Tissue was incubated with sterilization solution for 30 minutes with agitation. Samples were centrifuged and the supernatant was removed to remove sterilization solution. To rinse, sterile PBS was added to the tissue, samples were centrifuged, and supernatant was removed. Rinsing was repeated 3 times.

Testing.

Electron Microscopy

Samples were prepared for scanning electron microscopy (SEM) imaging by fixation in 0.1M sodium cacodylate buffer (2% glutaraldehyde and 2% paraformaldehyde (pH=7.35)). Samples were then dehydrated by microwaved graded ethyl alcohol rinses (20, 50, 70, 90, and 100%). Critical point drying in a Tousimis Auto-Samdri 815 automatic critical point dryer (Tousimis, Rockville, Md.) was performed, and samples were then placed on a carbon tape stub and sputter-coated with carbon using an Emitech K575X Peltier cooled sputter coater (Emitech, Houston, Tex.). An FEI Quanta 600FEG Environmental SEM (FEI Company, Hillsboro, Oreg.) was used for imaging and energy-dispersive x-ray spectroscopy (EDS).

Differential Scanning Calorimetry

Differential Scanning Calorimetry (DSC) was performed using a Q2000 DSC (TA Instruments, New Castle, Del.). Approximately 9-14 mg of homogenized tissue sample was sealed with 2 µL of deionized water in aluminum pans with a hermetic lid. Samples were run in triplicate (n=3) from −5° C. to 120° C. at a rate of 3° C.±0.64° C. per minute modulation every 80 seconds. Universal Analysis software integration tool was used to determine the onset denaturation temperature and denaturation temperature from the non-reversing heat flow signal.

Extrusion Force Testing

Each construct group was loaded into a syringe connected to a 20-gauge cannula. The syringes were secured into an Instron 584 Universal Testing Machine (Instron, Norwood, Mass.) in compressive mode. Force was measured over a constant rate of displacement. The syringes were run for 30 mm at a rate of 0.167 mm/second with force measurements taken every 0.1 second. Maximum extrusion force was taken from all compressive force data points over the 30 mm extension.

Cell Culture

L-929 murine fibroblast cells were purchased from ATCC (Manassas, Va.) and cultured at 37° C. and 5% $CO_2$ in Eagle's Minimum Essential Medium (EMEM) supplemented with 10% (v/v) horse serum and 200 U/mL Penn-Strep. Cells were subcultured and given fresh cell media as needed. All assays were conducted using L-929 murine fibroblast cells, and all assays were performed in a biological safety cabinet under sterile conditions.

Cell Viability and Proliferation Assay

A Quant-iT™ dsDNA® PicoGreen assay (Life Technologies, Grand Island, N.Y.) was performed using the manufacturer's protocol to measure cell proliferation. Homogenized tissue was added to a 96-well plate and seeded with $0.75 \times 10^4$ cells/mL with four replicates for each sample type (n=4). Cells were cultured for 3, 7, and 10 days with media changes every other day. Samples were removed from well plate, lyophilized, and digested with papain digestion buffer containing 125 µg/mL papain in PBE buffer containing sterile PBS with 5 mM cysteine-HCl and 5 mM $Na_2$ EDTA. The resulting digest, 1xTE buffer in DNase-free water, and the Quant-iT™ PicoGreen® dsDNA reagent (Invitrogen Corporation, Carlsbad, Calif.) were incubated away from light for 5 minutes. A Synergy H-1 Multi-Mode microplate reader (Biotek Instruments, Inc., Winooski, Vt.) was used to measure fluorescence intensity at 520 nm emission with 480 nm excitation. Double-stranded DNA (dsDNA) concentration was determined by interpolation from linear regression analysis using a five point lambda DNA standard.

ROS Assay

ROS activity was measured following the manufacturer's protocol for an OxiSelect™ ROS Assay kit (Cell Biolabs, Inc., San Diego, Calif.). Fibroblasts were seeded onto a 96-well plate at $3.7 \times 10^4$ cells/well in 200 $\mu$L of supplemented EMEM with five replicates for each sample type (n=5). Cells we allowed to become confluent overnight at 37° C. and 5% $CO_2$. Each well was rinsed with DPBS and 1×2', 7'-Dichlorodihydrofluorescin diacetate (DCF-DA)/EMEM was added. The plate was incubated for 1 hour at 37° C. and 5% $CO_2$. The 1×DCF-DA/EMEM was removed and wells were rinsed twice with DPBS. Each well had 50 $\mu$L of lyophilized homogenized tissue and 100 $\mu$L of EMEM added before incubation at 37° C. and 5% $CO_2$ for 12 hours. Cell lysis buffer was added to each well and incubated at room temperature for 5 minutes. Solution was transferred to a new 96-well plate and fluorescence intensity was read on a Synergy H-1 Multi-Mode microplate reader (Biotek Instruments, Inc., Winooski, Vt.) at 480 nm excitation and 530 nm emission. DCF concentration was determined by interpolation from linear regression analysis using an eight point DCF standard.

Cell Migration Assay

A CytoSelect™ Cell Migration assay (Cell BioLabs, San Diego, Calif.) was conducted according to the manufacturer's protocol. 50 µL of homogenized tissue and 100 µL serum-free media were added to each well of the lower chamber of a 96-well plate using a sterile 18-gauge cannula with eight replicated for each sample type (n=8). Fibroblasts were suspended in serum-free media and $2.5 \times 10^4$ cells were added to the upper chamber of each well with 100 µL of serum-free media. Cells were allowed to migrate across the membrane for 24 hours at 37° C. and 5% $CO_2$. Media was removed from the upper chamber and the upper chamber was removed from the bottom plate. The upper chamber was placed in the harvesting tray containing cell detachment solution and incubated for 30 minutes at 37° C. Cells were dislodged by gently tilting tray. Lysis Buffer/CyQuant GR dye solution was added to each well containing cells and detachment solution and incubated for 20 minutes at room temperature. Solutions were transferred to a new 96-well plate and read on a Synergy H-1 Multi-Mode microplate reader (Biotek Instruments, Inc., Winooski, Vt.) at 480 nm excitation and 520 nm emission. Cell migration is presented as the relative fluorescence intensity of a sample compared to wells with serum-free media only.

Statistical Analysis

Statistical analyses were conducted using SAS 9.4 software. A one-way analysis of variance (ANOVA) with a pair-wise Tukey test using the PROC GLM procedure was conducted to determine significant differences at a $p<0.05$ significance level. Linear regression analysis with a standard curve was to interpolate fluorescence intensity values and was conducted using the PROC REG procedure. Values from DSC, cell proliferation assays, ROS assays, and cell migration assays are presented as mean values+/−standard error of the mean calculated using Origin 9.1 software.

Electron Microscopy

Figure 1:
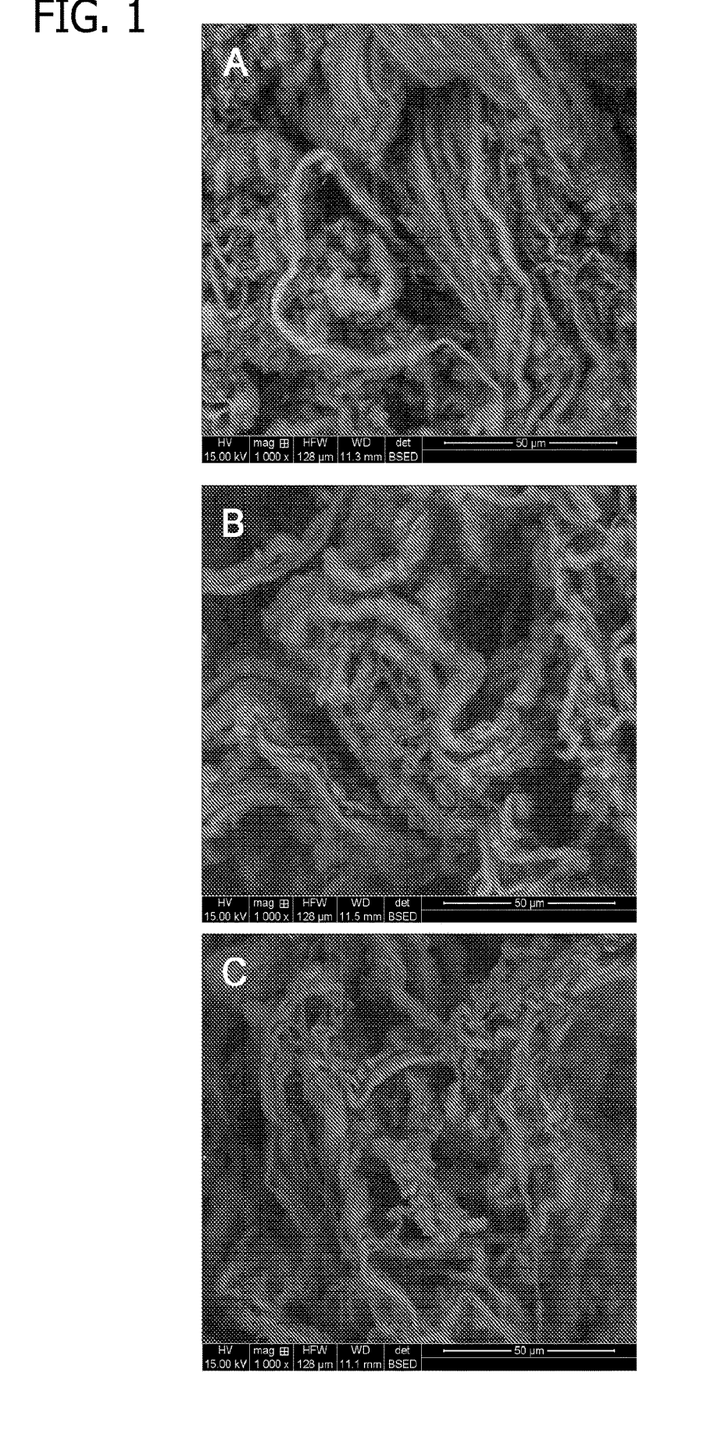
FIG. 1 shows SEM images of constructs confirming similar microstructure between construct types. All constructs demonstrate an open microstructure. (a) Decellularized construct. (b) Crosslinked construct (c) 4×100 nm construct.
Figure 2:
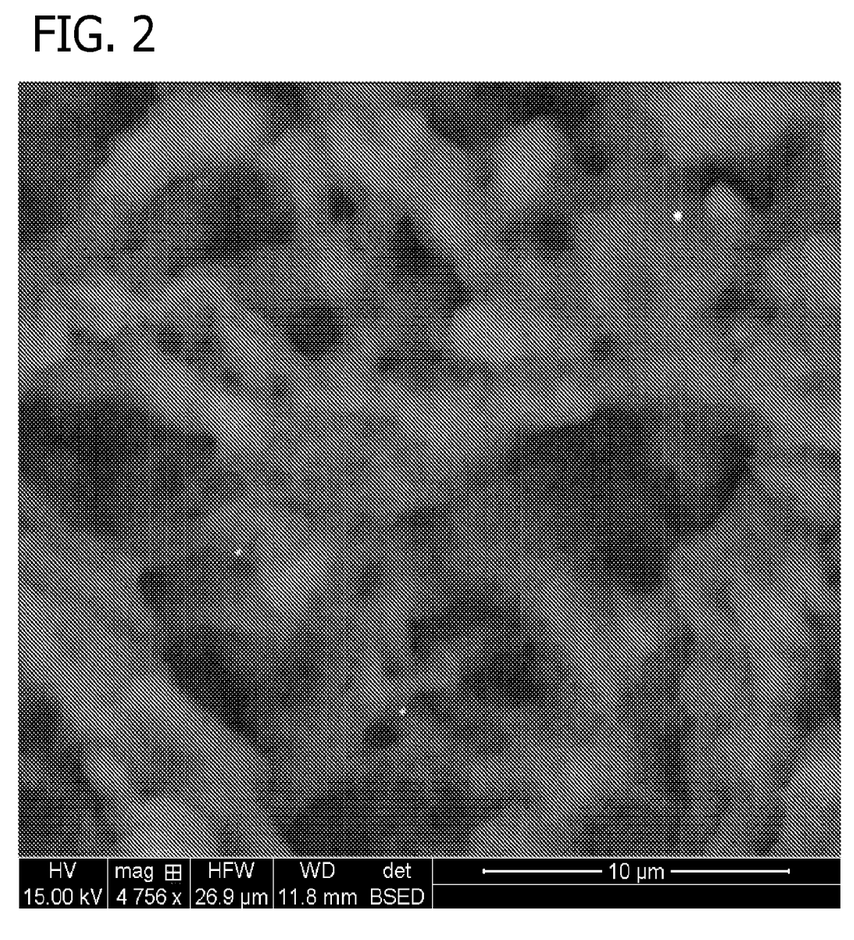
FIG. 2 shows SEM image of 1×100 nm construct confirming presence of gold nanoparticles (AuNP) by the presence of small, bright spheres within fainter ECM.

SEM and EDS analysis were conducted to confirm attachment of AuNP to homogenized tissue and to ensure that the treatment processes did not damage tissue. Refer to FIG. 1, which shows the open microstructure of constructs maintained during crosslinking and homogenization. Refer to FIG. 2, which confirms the attachment of AuNP to tissue. AuNP can be seen as small, bright circular features within fainter ECM. Features are confirmed to be AuNP by observing energy peaks at 2.1 keV and at 9.7 keV from EDS analysis.

SEM images and EDS analysis confirms an open microstructure of the constructs and attachment of AuNP to homogenized tissue. There are several advantages to attaching the AuNP to the tissue as opposed to incorporation by physical adsorption. Attachment prevents the AuNP from cellular uptake and from migration to other parts of the body. In addition, attachment prevents an immediate release of the AuNP allowing the construct to continually deliver the anti-inflammatory benefits of AuNP beyond initial implantation. SEM images demonstrate an open microstructure of the constructs that is important for cellular infiltration. Excessive crosslinking may limit the porosity of the constructs, reducing the ability for cells to infiltrate and remodel the tissue potentially leading to poor in vivo performance. It is also important to ensure that the processes of decellularization, crosslinking, homogenization, and sterilization do not damage the construct. SEM images reveal that the integrity of the ECM is retained through these processes.

Differential Scanning calorimetry

Figure 3:
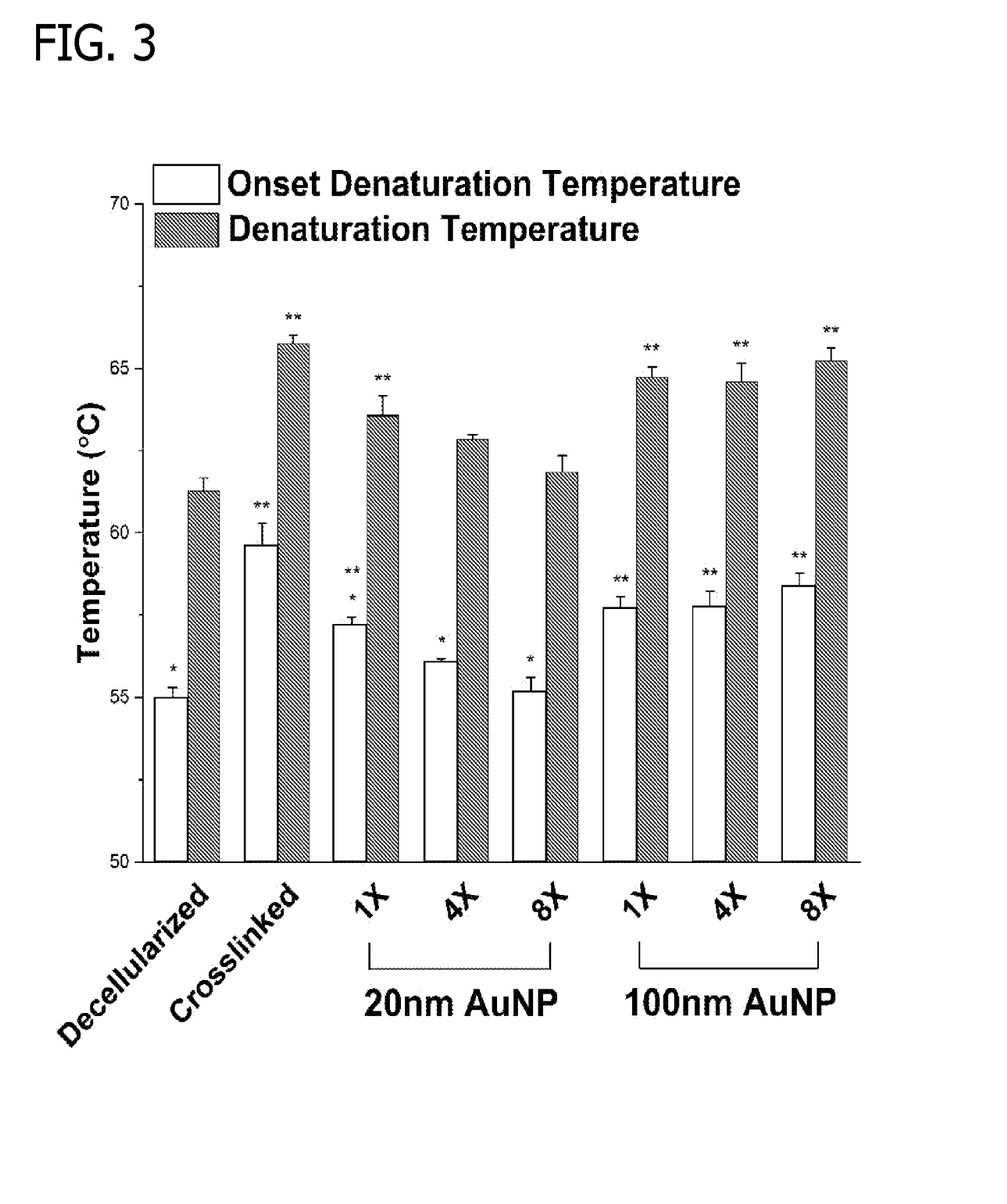
FIG. 3 shows differently scanning calorimetry (DSC) results showing onset denaturation temperature and denaturation temperature. *Indicates constructs with significantly lower mean temperatures compared to crosslinked constructs. **Indicates constructs with significantly higher mean temperatures than decellularized and 8×20 nm constructs. n=3. Error bars are given as standard error of the mean. p<0.05.

DSC testing was performed to analyze the thermal stability and degree of crosslinking of the constructs. Refer to FIG. 3, which gives DSC values for onset denaturation temperature and denaturation temperature. For onset denaturation temperature, crosslinked, 1×20 nm, 1×100 nm, 4×100 nm, and 8×100 nm constructs have significantly higher mean temperatures (n=3) than decellularized and 8×20 nm constructs. Crosslinked constructs have a significantly higher mean temperature than decellularized, 1×20 nm, 4×20 nm, and 8×20 nm constructs. In addition, 8×100 nm constructs have a higher mean temperature than the 4×20 nm constructs. For denaturation temperature, crosslinked, 1×20 nm, 1×100 nm, 4×100 nm, and 8×100 nm constructs have significantly higher mean denaturation temperatures than decellularized constructs. Crosslinked, 1×100 nm, 4×100 nm, and 8×100 nm constructs have significantly higher mean denaturation temperatures than 8×20 nm constructs. Crosslinked constructs have a significantly higher mean denaturation temperature than decellularized, 1×20 nm, 4×20 nm, and 8×20 nm constructs. In addition, 8×100 nm constructs have a higher mean denaturation temperature than 4×20 nm constructs.

Notable significant differences include crosslinked, 1×20 nm, 1×100 nm, 4×100 nm, and 8×100 nm constructs having significantly higher mean denaturation and onset denaturation temperatures compared to decellularized constructs. This difference confirms successful crosslinking since higher denaturation temperatures indicate a higher degree of crosslinking. Crosslinking may improve construct stability since low degrees of crosslinking are associated with more rapid in vivo degradation. On the other hand, excessive crosslinking can impede cell migration and cellular infiltration. It is important that the degree of crosslinking is sufficient enough to prevent quick degradation while still allowing cellular infiltration. Together, SEM images combined with denaturation temperatures confirm successful crosslinking while maintaining an open microstructure.

Crosslinked constructs have significantly higher mean denaturation and onset denaturation temperatures than 1×20 nm, 4×20 nm, and 8×20 nm constructs. This indicates that the addition of nanoparticles may ameliorate the potential excessive crosslinking that may occur during the crosslinking procedure. In addition, 8×20 nm constructs have significantly lower denaturation and onset denaturation temperatures than many of the other groups and were not statistically different than the decellularized group. This suggests that the larger 8× concentration of 20 nm AuNP further reduces crosslinking in the construct. This may be due to additional conjugation of 20 nm AuNP compared with 100 nm AuNP due to size differences between the AuNP.

Extrusion Force Testing

Extrusion force testing was performed to evaluate the ease of injection of the construct under forces and cannula gauges typically used for steroid injections into the knee. Extrusion force measurements of syringes filled with constructs were measured every 0.1 sec at a constant rate of displacement over 30 mm. Maximum extrusion forces were taken from all compressive force data points over the 30 mm extension and are presented in Table 1. The lowest maximum compressive force value is 1.72N and the highest is 3.82N.

TABLE 1

Extrusion force of homogenized tissue constructs through a 20 gauge cannula.

| Construct Type | Maximum extrusion force (N) |
| --- | --- |
| Decellularized | 1.72 |
| Crosslinked | 2.05 |
| 1x-20 nm | 3.82 |
| 4x-20 nm | 3.46 |
| 8x-20 nm | 1.81 |
| 1x-100 nm | 2.19 |
| 4x-100 nm | 3.15 |
| 8x-100 nm | 2.75 |

Particularly, a 20-gauge cannula was used to measure the extrusion force of all constructs. A gauge of 18-23 is commonly used for intra-articular injections of steroids into the knee. It is important to have a cannula that is large enough for the material to pass through while small enough for the physician to have control. In addition, the force required to eject the material should be minimal. If the size of the cannula is too small for the material to expel easily, it will require high forces to expel which may be dangerous to patients and physicians. Studies have shown that increasing the cannula size and the required force for injection has a negative effect on the physician's ability to control the syringe. A study was conducted on the extrusion forces of syringes expelled by rheumatoid arthritis patients with hand impairment. The average maximum force patients were able to apply during the injection was 33.21N and 45.34N for two different syringe types. The values found in our study of ~1 to 4 N are much less than those found in the cited study. In addition, the mean extrusion forces of porcine-collagen dermal fillers were measured to evaluate injectability. The study found that the lowest collagen dermal filler had a mean extrusion force of 7.7±0.5 N. This extrusion force was at an acceptable level to decrease clinician hand fatigue and to improve clinician hand control. All extrusion forces in this study were found to be less than the acceptable mean extrusion force found in the cited study. It is concluded that homogenized construct could be safely delivered using a 20-gauge cannula.

Cell Viability and Proliferation Assay

Figure 4:
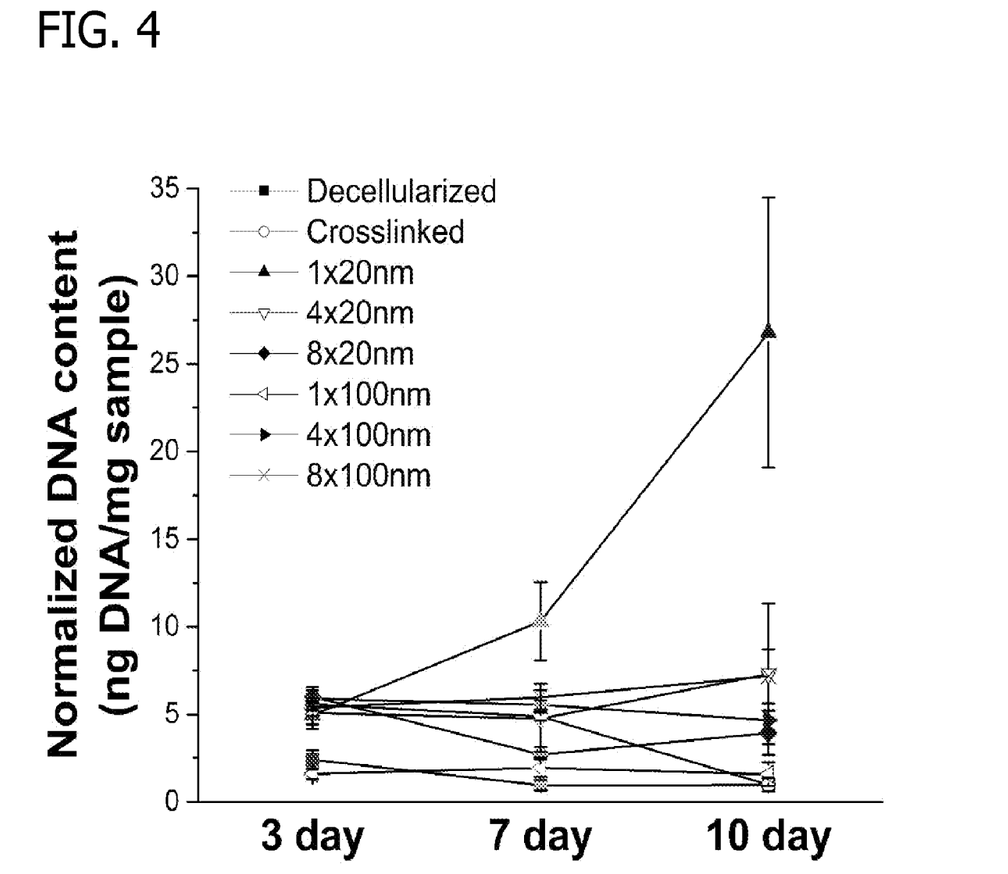
FIG. 4 shows PicoGreen assay results of constructs at 3, 7 and 10 day time points. *Indicates significantly higher DNA content compared to decellularized, crosslinked, 4×20 nm, 8×20 nm, and 1×100 nm constructs. ** Indicates significantly higher DNA content than decellularized, crosslinked, 4×20 nm, 8×20 nm, 1×100 nm, 4×100 nm, and 8×100 nm constructs. n=4. Error bars are given as standard error of the mean. p<0.05.

A cell viability and proliferation assay was performed to test the ability of fibroblasts to proliferate on the tissue constructs. Refer to FIG. 4, which provides the results of the 3, 7, and 10 day cell viability and proliferation assay. A PicoGreen dsDNA assay was used to determine dsDNA content of tissue constructs. The only significant difference within a single group between different days is that 1×20 nm constructs have a significantly higher mean dsDNA content (n=4) at 10 days compared to 1×20 nm constructs at both 3 and 7 days. At 3 days, crosslinked, 4×20 nm, 8×20 nm, 4×100 nm, and 8×100 nm constructs have significantly higher mean dsDNA contents than decellularized constructs. Crosslinked, 1×20 nm, 4×20 nm, 8×20 nm, 4×100 nm, and 8×100 nm constructs have a significantly higher mean dsDNA content than 1×100 nm constructs at 3 days. At 7 days, 1×20 nm constructs have a significantly higher mean dsDNA content than decellularized, crosslinked, 4×20 nm, 8×20 nm, and 1×100 nm constructs. 8×100 nm constructs have a significantly higher mean dsDNA content than decellularized constructs at 7 days. At 10 days, 1×20 nm constructs have a significantly higher dsDNA content than decellularized, crosslinked, 4×20 nm, 8×20 nm, 1×100 nm, 4×100 nm, and 8×100 nm constructs.

Cell proliferation is seen as viability increases from progressive time points. The fact that only 1×20 nm constructs showed a significant increase in cell viability from 3 to 7 and 3 to 10 days demonstrates that less cell proliferation occurred on other groups compared to the 1×20 nm constructs. Cell viability can be interpreted from the PiCoGreen dsDNA assay by comparing the dsDNA content of construct groups at individual time points. At 3 days, crosslinked constructs and 4× and 8× concentrations of both 20 nm and 100 nm AuNP constructs have a higher cell viability than decellularized constructs. This indicates a potential benefit of crosslinking the tissue and well as using higher concentrations of both 20 nm and 100 nm AuNP. In addition, at 3 days, 4×100 nm and 8×100 nm constructs have a significantly higher cell viability than 1×100 nm constructs. This result also suggests a possible cell viability benefit of using higher concentrations of 100 nm AuNP. At 7 days, 1×20 nm had a significantly higher cell viability than decellularized, crosslinked, 4×20 nm, 8×20 nm, and 1×100 nm constructs leading to several conclusions. First, at 7 days the 1×20 nm constructs maintained the higher cell viability compared with decellularized and crosslinked constructs present at 3 days. Second, at the same concentration, 1×20 nm constructs have a higher cell viability than 1×100 nm constructs demonstrating superior performance of 20 nm AuNP constructs compared to 100 nm AuNP constructs at a 1× concentration. The benefit of 20 nm AuNP may occur at a lower concentration than for 100 nm AuNP. In addition, the use of higher concentrations of 20 nm AuNP on constructs does not increase cell viability. Lastly, 8×100 nm constructs had a significantly higher cell viability than crosslinked constructs at 7 days. This indicates that it may take higher concentrations of 100 nm AuNP to see an improvement in cell viability. At 10 days, 1×20 nm constructs had a significantly higher cell viability compared to decellularized, crosslinked, 4×20 nm, 8×20 nm, 1×100 nm, 4×100 nm, and 8×100 nm constructs. The 10 day time point builds on the 7 day time point that 1×20 nm constructs show an increase over all other tissue constructs and there may be an advantage to using this 1×20 nm constructs to increase cell viability.

There are several reasons why the 1×20 nm constructs showed superior cell viability and were the only constructs to demonstrate cell proliferation. Cell adhesion is necessary for fibroblast proliferation. The topography of a surface will affect the degree of adhesion of the cells to a surface. It has been shown that AuNP of particular sizes affect cell adhesion by creating a topography favoring cellular adhesion. The 1×20 nm constructs in this study may have provided a more favorable surface for cellular adhesion compared to other constructs. In a recent study by Zhu et al., mouse fibroblasts favored adhesion on surfaces containing 35 nm AuNP. Both the size and concentration of AuNP will affect the surface that the cell interacts with which ultimately affects cell adhesion.

ROS Assay

Figure 5:
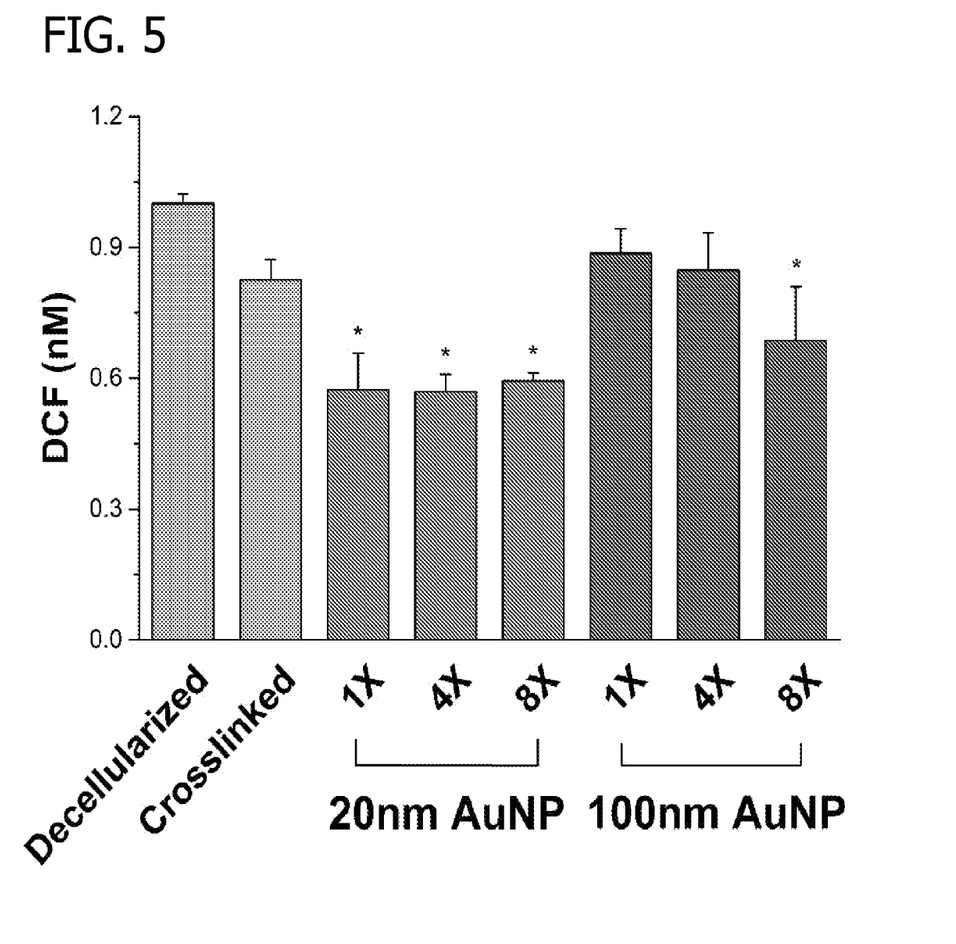
FIG. 5 shows intracellular ROS assay results for constructs. DCF concentration directly corresponds to intracellular ROS levels. *Indicates significantly lower DCF concentration compared to decellularized constructs. n=5. Error bars are given as standard error of the mean. p<0.05.

Refer to FIG. 5, which provides the ROS assay results. An OxiSelect™ ROS Assay kit was used calculate the relative DCF concentration of cells cultured with tissue constructs that directly correlates to ROS concentration. 1×20 nm, 4×20 nm, 8×20 nm, and 8×100 nm constructs have significantly lower mean DCF concentrations than decellularized constructs (n=5). Additionally, 4×20 nm constructs have a significantly lower mean DCF concentration compared to 1×100 nm constructs.

Oxidative stress has the potential to induce cell and tissue damage by activating cellular pathways leading to inflammation, apoptosis, and negative effects on remodeling and cell proliferation. The reduction of damaging ROS is important for the promotion of remodeling. AuNP have been used as an anti-inflammatory agent due to AuNP's ability to act as free radical scavengers. Reduction in cellular ROS due to AuNP has been shown to be concentration dependent. Similar to the effects of proliferation and migration, the concentration and size of the nanoparticle affects how the cells interact with the particles. Previous studies of cellular ROS concentrations on collagen-100 nm AuNP constructs have shown a concentration dependent decrease in ROS production. Too high of a concentration of nanoparticles may induce toxicity or disruptive effects to cellular events. Too low of a concentration of nanoparticles may not be sufficient for cells to recognize or to have a beneficial effect. This study showed a reduction in ROS levels for constructs at all concentrations of 20 nm AuNP and for 1×100 nm constructs compared to decellularized constructs. It is possible that using a 1× concentration of 100 nm AuNP is the upper concentration limit for free radical scavenging ability of 100 nm AuNP constructs. 20 nm AuNP showed decreased ROS at all concentrations suggesting that even at higher concentrations, 20 nm AuNP can still provide anti-oxidative effects. More studies need to be conducted to investigate the exact mechanism of the reduction of ROS by AuNP to more effectively tune the size and concentration of AuNP to be used for anti-inflammatory agents.

Cell Migration Assay

Figure 6:
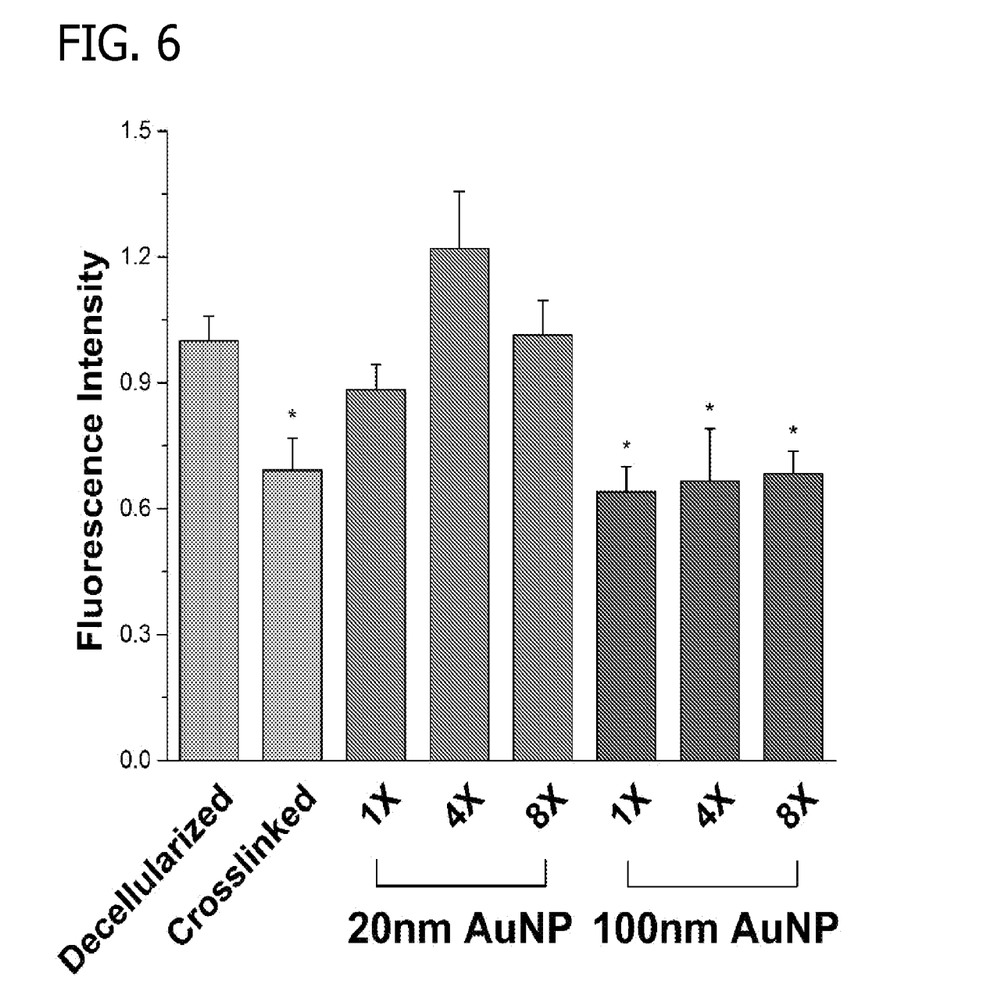
FIG. 6 shows migration assay results for constructs. Fluorescence intensity directly corresponds to migrated cell concentration. *Indicates constructs with significantly lower fluorescence intensity compared to 4×20 nm. n=8. Error bars are given as standard error of the mean. p<0.05.

Refer to FIG. 6, which provides the migration assay results. A CytoSelect™ Cell Migration assay was conducted using homogenized tissue constructs as a chemoattractant and the relative amount of migrated cells was measured by fluorescence intensity. There is a significantly higher mean fluorescence intensity on 4×20 nm constructs compared to crosslinked, 1×100 nm, 4×100 nm, and 8×100 nm constructs (n=8).

Cell migration is influenced by a variety of factors including cell type and nanoparticle characteristics. ECM has been shown to be a chemoattractant for cells as part of a constructive remodeling process. To further enhance the cell migration potential of the construct, AuNP were conjugated to the ECM prior to homogenization. It is known that the migration of cells to nanoparticles depends on the nanoparticle size as well as cell type. A recent study by Hung et al. demonstrated that nanocomposites of collagen and 5 nm AuNP promoted enhanced migration of MSC's although it is not well known how AuNP modulate the effect. In a study by Yang et al., migration of human dermal fibroblasts in the presence of 90 nm AuNP was increased compare to cells without Fibroblast cells have complex cytoskeletal networks that use lamellipodia to adhere to surfaces and regulate cell migration. These types of cells are more susceptible to differences in AuNP charge, size and shape due to the microtubule networks. Cell migration assay results demonstrated a higher indication of migrated cells towards 4×20 nm constructs compared to crosslinked and all concentrations of 100 nm AuNP constructs (FIG. 6). It may be possible that the 4×20 nm constructs promote a more favorable point of contact for cells compared with the 100 nm AuNP, increasing attachment to facilitate migration.

In summary, results support that constructs conjugated with AuNP demonstrate superior in vitro performance over constructs without nanoparticles. Further, 20 nm AuNP appear to have enhanced cell viability, cell proliferation, ROS reduction and cell migration induction over 100 nm AuNP at varying concentrations. Future studies involve further optimization of nanoparticle concentration and evaluation of in vivo performance.

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

The invention claimed is:

1. An injectable bionanocomposite comprising a homogenized nanoparticle-bioscaffold, wherein the bioscaffold comprises a decellularized tissue, the decellularized tissue being conjugated with a nanoparticle and subsequently homogenized to produce the injectable bionanocomposite; wherein the nanoparticle is metallic, ceramic, polymeric or a combination thereof; and wherein the bionanocomposite has an extrusion force from about 0.5 N to about 10 N as measured in a 20-gauge cannula.

2. The injectable bionanocomposite of claim 1, wherein the decellularized tissue is porcine or human tissue.

3. The injectable bionanocomposite of claim 1, wherein the nanoparticle comprises an amine-functionalized gold nanoparticle (AuNP).

4. The injectable bionanocomposite of claim 1, wherein the nanoparticle comprises a hydroxyapatite nanoparticle.

5. The injectable bionanocomposite of claim 1, wherein the nanoparticle comprises a silver nanoparticle.

6. The injectable bionanocomposite of claim 1, wherein the denaturation temperature of the bionanocomposite increases upon conjugation with a nanoparticle as compared to decellularized tissue not conjugated with a nanoparticle.

7. The injectable bionanocomposite of claim 1, wherein the extrusion force measured in a 20-gauge cannula is from about 0.5 N to about 5 N.

8. The injectable bionanocomposite of claim 1, wherein the extrusion force measured in a 20-gauge cannula is from about 1 N to about 4 N.

9. The injectable bionanocomposite of claim 1, wherein the cell viability measured using a dsDNA assay is increased as compared to decellularized tissue not conjugated with a nanoparticle.

10. The injectable bionanocomposite of claim 1, wherein the decellularized tissue is a meniscus, a tendon, a ligament, a diaphragm, or a combination thereof.

11. The injectable bionanocomposite of claim 10, wherein the decellularized tissue comprises a diaphragm.

12. A method of treating osteoarthritis comprising administering an effective amount of the bionanocomposite of claim 1 to a subject in need thereof by injection into the affected area.

13. The method of claim 12, wherein the osteoarthritis is post-traumatic osteoarthritis.

14. The method of claim 12, wherein the affected area is a joint.

15. The method of claim 14, wherein the joint is a knee, an ankle, a hip, a wrist, an elbow, a knuckle, a shoulder, or a combination thereof.

16. A method of treating tissue degradation comprising administering an effective amount of the bionanocomposite of claim 1 to a subject in need thereof by injection to the subject's heart, disc, muscle, urinary tract, adipose tissue, meniscus, ligament, tendon, or a combination thereof.

17. A method for fabricating an injectable bionanocomposite of claim 1, comprising:
- decellularizing a biological tissue to produce a decellularized tissue,
- conjugating the decellularized tissue with a nanoparticle to produce a nanoparticle-bioscaffold, and
- homogenizing the nanoparticle-bioscaffold to produce the injectable bionanocomposite with an extrusion force from about 0.5 N to about 10 N as measured in a 20-gauge cannula.

* * * * *